United States Patent [19]

Schäfer et al.

[11] Patent Number: 5,739,328

[45] Date of Patent: Apr. 14, 1998

[54] PREPARATION OF ASYMMETRICALLY SUBSTITUTED TRIAZINES

[75] Inventors: Bernd Schäfer, Dierbach; Horst Mayer, Ludwigshafen, both of Germany

[73] Assignee: BASF Aktiengesellschaft, Ludwigshafen, Germany

[21] Appl. No.: 619,667

[22] PCT Filed: Oct. 10, 1994

[86] PCT No.: PCT/EP94/03331

§ 371 Date: Mar. 29, 1996

§ 102(e) Date: Mar. 29, 1996

[87] PCT Pub. No.: WO95/11237

PCT Pub. Date: Apr. 27, 1995

[30] Foreign Application Priority Data

Oct. 19, 1993 [DE] Germany .................. 43 35 497.1

[51] Int. Cl.$^6$ .................................................. C07D 251/46
[52] U.S. Cl. .................................... 544/194; 544/211
[58] Field of Search .............................. 544/194, 211

[56] References Cited

U.S. PATENT DOCUMENTS 3,360,534  12/1967  Odo ........................................ 260/429.9
4,886,881  12/1989  Chiang .................................... 544/194

FOREIGN PATENT DOCUMENTS 252 374  12/1987  Germany .
167 500  11/1990  India .

OTHER PUBLICATIONS

Yakugaku Zashi 95, 499–511 (1975)—English translation.
Dutta et al., Coord. Chem. Rev., 1967, 441–457.
Chem. of Heterocyclic Compounds, Nov. 1989, 547–550, vol. 25, No. 5.

*Primary Examiner*—John M. Ford

*Attorney, Agent, or Firm*—Keil & Weinkauf

[57] ABSTRACT

A process for preparing asymmetrically substituted triazines of the formula I

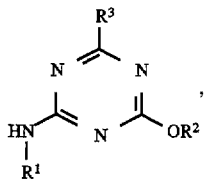

where $R^1$ is hydrogen, methyl or ethyl, $R^2$ and $R^3$ independently of one another are an unsubstituted or substituted hydrocarbon radical, by reaction of a cyanoguanidine of the formula II

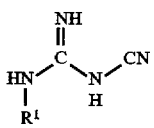

with a carboxylic acid derivative in the presence of an alcohol of the formula III $R^2$—OH     III, which comprises reacting a carboxylic acid ester of the formula IV $R^3$—COOR$^4$     IV, where $R^3$ has the abovementioned meaning and $R^4$ is an unsubstituted or substituted hydrocarbon radical, in the presence of a base or of a carboxamide selected from the group consisting of N,N-dialkylformamide, N,N-dialkylacetamide and N-methylpyrrolidone and in the presence of a salt or of a salt-like compound of the elements magnesium, calcium, aluminum, zinc, copper, iron, cobalt, nickel or chromium, is described.

13 Claims, No Drawings

PREPARATION OF ASYMMETRICALLY SUBSTITUTED TRIAZINES

This is a 371 of PCT/EP84/03331, filed Oct. 10, 1994.

BACKGROUND OF THE INVENTION

1. Field of the Invention

The present invention relates to a process for preparing asymmetrically substituted triazines of the general formula I

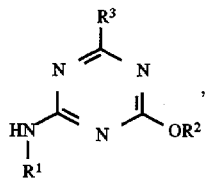

where $R^1$ is hydrogen, methyl or ethyl, $R^2$ and $R^3$ independently of one another are a hydrocarbon radical having 1 to 6 C atoms, which can carry substituents which are inert under the reaction conditions, by reaction of a cyanoguanidine of the formula II

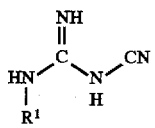

with a carboxylic acid derivative in the presence of an alcohol of the formula III $$R^2\text{—OH} \quad\quad\quad \text{III}$$

2. Description of Related Art

Asymmetrically substituted triazines can be prepared in a great variety of ways, eg. starting from N-cyanoamides by reaction with Vilsmeier complexes (R. L. N. Harries, Aust. J. Chem. 34 (1981) 623), from N-cyanoimidate esters (DE-A 34 11 202; M. A. Pérez, J. L. Soto, Heterocycles, 20 (1983) 463; K. R. Huffman, F. C. Schaefer, J. Org. Chem. 28 (1963) 1816) or from biguanidines (S. L. Shapiro et al, J. Org. Chem. 25 (1960) 379; U.S. Pat. No. 2,535,968). The reaction of guanylthiourea with dimethyl sulfate and carboxylic acid derivatives has also been published (H. Eilingsfeld, H. Scheuermann, Chem. Ber. 100 (1967) 1874; DE-A 16 70 147; EP-A 545 149) as well as the reaction of trichloroacetamidinoguanidines with derivatives of trifluoroacetic acid (DE-A 40 34 078). According to all these methods, no chelate complexes are passed through as intermediates.

Another possibility for preparing 6-trifluoromethyl-1,3,5-triazines according to a process known from Yakugaku Zasshi 95, (1975) 499–511 consists in converting N-cyanoguanidines into copper complexes of N-amidino-O-alkylisoureas, liberating the urea derivatives with hydrogen sulfide and then reacting them with trifluoroacetate esters according to the following reaction scheme:

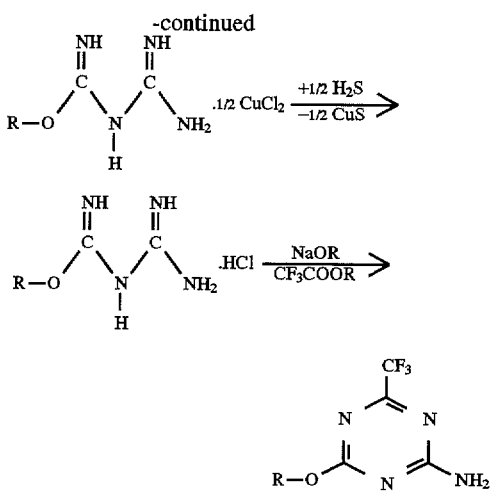

A variant of this process is known from DD-A-252 374, the acetate of copper being used instead of copper(II) chloride.

Stoichiometric amounts of Cu salts are necessary for this process; in the absence of Cu salts, mainly guanylurea is formed instead of the N-amidino-O-alkylisourea (Kyushu Kogyo Daigaku Kenkyu Hokoku No. 12, (1962) 69–78).

The reaction of N-amidino-O-alkylisourea hydrochloride with ethyl chloroacetate in ethanol/NaOC$_2$H$_5$ leads to the corresponding chloromethyltriazine only in poor yields. The starting material has to be set free from the Cu complex beforehand.

The preparation of chelate complexes starting from cyanoguanidine using copper acetate or zinc chloride in methanol is described by R. I. Dutta and A. Syamal in Coord. Chem. Rev., Vol. 2, 1967, pp. 441–457. It is known from Chemistry of Heterocyclic Compounds, Vol. 25, 1989, pp. 547–550 to isolate zinc complexes of this type and then to react them with trifluoroacetic anhydride to give the triazine.

In a similar manner, zinc sulfate forms a chelate complex which after working up by boiling in water decomposes in a second reaction step to give the sulfate of amidino-O-methylisourea (U.S. Pat. No. 3,360,534, IN-A 167 500) and this can be reacted in a third reaction step with acetic anhydride (S. Lotz, G. Kiel, G. Gattow, Z. anorg. allg. Chem. 604 (1991) 53–62) or with methyl trifluoroacetate (T. Tsujikawa, Yakugaku Zasshi 95, loc. cit) to give the triazine in yields of 31 and 26% respectively.

The last-mentioned processes are always very laborious multistage processes which in the case of the esters lead to the desired triazines only in poor yields or in the case of the anhydrides inevitably include the production of stoichiometric amounts of carboxylic acid which can only be recycled to give the corresponding anhydrides very laboriously. As a rule, the toxicologically unacceptable, occasionally poorly filterable heavy metal complexes have to be isolated and then reacted with the anhydrides in an inert solvent, as reaction in alcoholic solution is prevented on account of the reaction of anhydrides with alcohols. In addition, the processes described are disadvantageous inasmuch as unavoidably large amounts of heavy metal salts are obtained in the form of organic slurries which can only be disposed of with difficulty.

U.S. Pat. No. 4,886,881 describes the single stage synthesis of 2-aminotriazines, starting from cyanoguanidine and trimethyl orthoacetate in the presence of a Lewis acid catalyst such as zinc chloride. Dimethylformamide and acetonitrile are recommended as solvents.

It is an object of the present invention to find a process which makes available triazines of the structure I by reaction of cyanoguanidines with carboxylic acid esters which are more readily available but also less reactive than corresponding anhydrides or orthoesters. If possible, this process is intended to be carried out without isolation of intermediates (one-pot process).

SUMMARY OF THE INVENTION

We have found that this object is achieved by a process for preparing asymmetrically substituted triazines of the general formula I

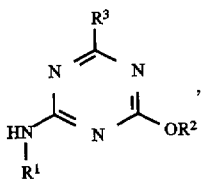

where $R^1$ is hydrogen, methyl or ethyl, $R^2$ and $R^3$ independently of one another are a hydrocarbon radical having 1 to 6 C atoms, which can carry substituents which are inert under the reaction conditions, by reaction of a cyanoguanidine of the formula II

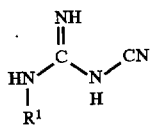

with a carboxylic acid derivative in the presence of an alcohol of the formula III

which comprises reacting a carboxylic acid ester of the formula IV

where $R^3$ has the abovementioned meaning and $R^4$ is a hydrocarbon radical having 1 to 6 C atoms, which can carry substituents which are inert under the reaction conditions, in the presence of a base or of a carboxamide selected from the group consisting of N,N-di($C_1$-$C_4$-alkyl)formamide, N,N-di($C_1$-$C_4$-alkyl)acetamide and N-methylpyrrolidone and in the presence of a salt or of a salt-like compound of the elements magnesium, calcium, aluminum, zinc, copper, iron, cobalt, nickel or chromium.

DESCRIPTION OF PREFERRED EMBODIMENTS

The substituted cyanoguanidine used as a starting substance is generally known. The N-methyl- and N-ethyl-substituted derivatives are available from cyanoguanidine and dialkyl sulfate as described by A. E. Kretov and A. S. Bespalyi in Zhur. Prik. Khimii, Vol. 34, (1961) 621ff. The guanidine can also be employed in the form of an acid addition salt, in this case the acid set free during the reaction expediently being neutralized by addition of a suitable base such as sodium methoxide.

As the hydrocarbon radical in the triazine I, aliphatic, cycloaliphatic, aromatic or araliphatic radicals having up to 8 carbon atoms such as $C_1$-$C_8$-alkyl, $C_3$-$C_8$-alkenyl, $C_3$-$C_8$-alkynyl, $C_3$-$C_8$-cycloalkyl and also phenyl, benzyl or phenethyl are to be mentioned in particular for $R^2$. With respect to the use of the intermediates I to be prepared, $R^2$ is, for example, $C_1$-$C_4$-alkyl such as methyl, ethyl, n-propyl, isopropyl, n-butyl, sec-butyl or tert-butyl; $C_3$-$C_4$-alkenyl such as prop-2-en-1-yl, 1-methylprop-2-en-1-yl, but-2-en-1-yl or but-3-en-1-yl; $C_3$-$C_4$-alkynyl such as prop-2-yn-1-yl or but-2-yn-1-yl; $C_3$-$C_6$-cycloalkyl such as cyclopropyl, cyclobutyl, cyclopentyl or cyclohexyl; particularly preferably $C_1$-$C_4$-alkyl such as methyl.

The radical $R^2$ can in turn carry still further substituents which are inert under the reaction conditions, such as eg. fluorine or chlorine, phenyl, $C_1$-$C_4$-alkyl, $C_1$-$C_4$-haloalkyl or $C_1$-$C_4$-alkoxy.

The carboxylic acid ester radical $R^4$ has the meaning mentioned above for $R^2$ and is preferably identical to $R^2$.

According to observations to date, the radical $R^3$ is widely variable. It can have eg. the meanings specifically mentioned for $R^2$. With respect to the intended use of the triazines I, $R^3$ is preferably $C_1$-$C_4$-haloalkyl, in particular fluoro- or chloromethyl or -ethyl such as $CCl_3$, $CF_3$, $CF_2CF_3$, $CF_2Cl$, $CFCl_2$, $CH_2Cl$, $CHCl_2$, $CH_2F$ and $CHF_2$. Perhalogenated alkyl radicals such as $CCl_3$, $CF_3$ and $C_2F_5$ are particularly preferred.

According to the invention, the reaction of the cyanoguanidine II with the alcohol III (or $R^4OH$, formed by hydrolysis of the ester IV) is carried out in the presence of a base. Surprisingly, the reactivity of the metal chelate complexes can be increased by this means such that the reaction with the esters IV is possible, even though these esters are less reactive by far than corresponding carboxylic anhydrides or orthoesters.

Suitable bases are inorganic and organic bases. Preferred inorganic bases are alkali metal and alkaline earth metal hydroxides, and preferred organic bases are tertiary amines such as $C_1$-$C_4$-trialkylamine, eg. triethylamine, pyridine or N-methylmorpholine. The alkali metal or alkaline earth metal alkoxide of the alcohol $R^2OH$ to be reacted is expediently used as a base. This alkoxide can also be formed in situ, eg. from the corresponding alkali metal or sodium amide or sodium hydride and the alcohol III.

The amount of base is customarily from 0.1 to 2, in particular from 0.8 to 1.2, mole equivalents, based on the cyanoguanidine II. Larger amounts are possible, but as a rule provide no further advantages.

A carboxamide from the group consisting of N,N-di($C_1$-$C_4$-alkyl)formamide, N,N-di($C_1$-$C_4$-alkyl)acetamide or N-methylpyrrolidone can also be used instead of the base or additionally. Examples which may be mentioned are dimethylformamide, diethylformamide, dimethylacetamide and diethylacetamide. The addition of carboxamides has proven particularly suitable when using heavy metals, in particular copper, as chelating agents.

The amount of carboxamide is in general from 1 to 30, in particular from 5 to 10, mole equivalents, based on the cyanoguanidine II. It may also be advantageous to utilize the carboxamide as a solvent.

Suitable salts or salt-like compounds of the alkaline earth metals, of aluminum or of the heavy metals are products readily soluble in the reaction medium, such as halides, eg. fluorides, chlorides or bromides, nitrates, sulfates or possibly phosphates, alkoxides or acetates. According to present knowledge, apart from good solubility the type of alkaline earth metal compound or metal compound does not matter, so that, inter alia, cost considerations are decisive in the choice. Examples which may be listed are the following compounds: $MgCl_2$, $Mg(OCH_3)_2$, $CaCl_2$, $Zn(NO_3)_2$, $Cu(CH_3COO)_2$, $AlCl_3$, $AlBr_3$, $ZnCl_2$, $ZnBr_2$, $CuCl_2$, $NiBr_2$, $CrCl_3$, CaO, $Ca(NO_3)_2$, $MS(NO_3)_2$, MgO, ZnO, $FeCl_2$, $FeCl_3$, $Fe(NO_3)_2$, $Fe(NO_3)_3$. The chlorides, in particular $CaCl_2$ and $ZnCl_2$, are particularly preferred.

One advantage of the process according to the invention is that the presence of heavy metals can be largely or completely dispensed with and, for ecotoxicological reasons, less unacceptable elements such as magnesium and in particular calcium can be avoided. Soluble salts of these elements are therefore particularly preferred. Very good results are also achieved, however, with zinc compounds.

The salts or salt-like compounds of the abovementioned elements can be employed in stoichiometric amounts or preferably less than stoichiometric amounts, based on the cyanoguanidine II, eg. in amounts of from 0.001 to 2 mol, in particular from 0.005 to 1.0 mol per mole of II.

When using heavy metals, their amount is kept as low as possible and only catalytic amounts, eg. under 0.6 mol, are employed per mole of cyanoguanidine. In the case of magnesium and calcium salts, the particularly preferred amount is from 0.01 to 1.0, in particular from 0.05 to 0.5 mol. Of course, more than stoichiometric amounts, based on II, eg. from 1 to 2 mol per mole of II, can be employed, but reasons of economy are a point in favor rather of employing substoichiometric amounts.

On the one hand, the starting substance III can be formed in situ from the carboxylic acid ester IV ($R^2=R^4$) or is added to the reaction mixture (preferably as a solvent). When using the starting material III simultaneously as a solvent, it is recommended to select the alcohol component in the ester IV accordingly (ie. $R^2=R^4$) in order to avoid by-products.

The molar ratio of cyanoguanidine II to the alcohol III is in general from 1 to 30, in particular from 5 to 10.

The carboxylic acid ester IV is expediently used in an amount of from 0.5 to 10, in particular from 1 to 5 mol, per mole of cyanoguanidine II. The esters IV to be mentioned are particularly preferably the following compounds:

$C_1$–$C_4$-alkane- or haloalkanecarboxylic acid esters such as methyl acetate, ethyl acetate, methyl propionate, ethyl propionate, methyl trifluoroacetate, methyl difluoroacetate, methyl fluoroacetate, methyl trichloroacetate, methyl dichloroacetate, methyl chloroacetate, ethyl trifluoroacetate, (m)ethyl pentafluoropropionate and (m)ethyl pentachloropropionate. With respect to the intended use of the triazines I as intermediates for crop protection agents, methyl trifluoroacetate and ethyl trifluoroacetate are particularly preferred as starting substances IV.

The reaction of II with III and IV can be carried out in substance, ie. without addition of inert solvents. Advantageously, the alcohol $R^2OH$ is simultaneously used as a solvent. According to a particularly preferred embodiment, the corresponding alkoxide is then selected as a base.

The reaction temperature is from 0° to 200° C., in particular from 20° to 150° C., particularly preferably the reflux temperature of the reaction mixture.

Particular conditions with respect to the pressure are not necessary, in general the reaction is carried out at atmospheric pressure or under the autogenous pressure of the particular reaction medium.

The reaction can be carried out continuously and also batchwise. In the continuous procedure the reaction components are preferably passed through a tubular reactor or a stirred tank reactor cascade.

According to a particularly preferred embodiment of the process according to the invention, the triazine I is prepared without isolation of intermediates. For example by initially introducing the cyanoguanidine II, the ester IV and less than the stoichiometric amounts of the alkaline earth metal salt or of the metal salt (or salt-like compounds) into the alcohol $R^2OH$ as a solvent, metering in the base, eg. the alkali metal alkoxide such as $NaOR^2$ or $KOR^2$ and heating the mixture to reflux.

As a rule, the reaction is terminated in a customary manner when cyanoguanidine can no longer be detected in the reaction mixture (eg. by means of thin-layer chromatography, high pressure liquid chromatography or gas chromatography).

Working-up to the process product I is then as a rule carried out by conventional processes such as distillation, filtration, centrifugation or by addition of water and subsequent extraction.

The crude products obtained can be further purified if desired, eg. by crystallization, rectification or by means of chromatographic methods.

The triazines I which can be prepared in a simple manner by the process according to the invention are useful intermediates for the synthesis of dyestuffs, drugs and crop protection agents, in particular herbicides, as described eg. in the publications EP-A 508 348, EP-A 111 442 or DE-A 40 38 430.

SYNTHESIS EXAMPLES

Example 1

2-Amino-4-methoxy-6-trifluoromethyl-1,3,5-triazine 21 g (0.25 mol) of N-cyanoguanidine, 3.4 g (0.025 mol) of anhydrous zinc chloride and 160 g (1.25 mol) of methyl trifluoroacetate are initially introduced into 400 ml of methanol, the mixture is warmed to 50° C. and 50 g (0.27 mol) of 30% strength sodium methoxide solution are pumped in in the course of 10 hours. The solvent is then largely removed, and the residue is washed with 250 ml of water and 250 ml of dilute hydrochloric acid and dried at 60° C./20 mbar. 43.2 g (0.22 mol, 89%) of 2-amino-4-trifluoromethyl-6-methoxy-1,3,5-triazine are obtained in the form of a colorless powder (HPLC: >99% by weight) M.p.: 161°–163.5° C.

Example 2

2-Amino-4-methoxy-6-trifluoromethyl-1,3,5-triazine 56.6 g (0.5 mol) of calcium chloride (98%, powdered) and 210 g (2.5 mol) of N-cyanoguanidine are initially introduced into 2 l of methanol. The mixture is heated with stirring to reflux temperature and stirred under reflux for one hour, whereupon a homogeneous solution is obtained. The mixture is then cooled to room temperature and 640 g (5.0 mol) of methyl trifluoroacetate and then, in the course of 25 minutes, 450 g (2.5 mol) of a solution of sodium methoxide (30% by weight in methanol) are added, whereupon a white precipitate deposits. After heating under reflux for 2 hours, the mixture is cooled to room temperature and a pH of about 6 is set by addition of conc. hydrochloric acid. The methanol is then distilled off, about 2 l of water are added little by little, and the deposited, finely crystalline white crystals are separated off and dried in vacuo.

Yield: 402.4 g (2.07 mol; 83% of theory).

$^1$H-NMR spectrum (270 MHz, $CDCl_3$, int. TMS, δ (ppm)):
6.45 br (1H); 5.88 br (1H); 4.03 s (3H).

Example 3

2-Amino-4-methoxy-6-trifluoromethyl-1,3,5-triazine 84 g (1 mol) of cyanoguanidine and 100 g (0.5 mol) of copper acetate are initially introduced into 600 ml of methanol and the mixture is heated to reflux for 7 h. After cooling to 20° C., the mixture is filtered with suction and the solid copper complex is separated off and dried in vacuo. 41.4 g (0.1 mol) of this residue are initially introduced into 200 ml of methanol and 45 g (0.25 mol) of 30% strength sodium methoxide solution are added dropwise in the course of 15 min. 76.8 g (0.6 mol) of methyl trifluoroacetate are then added dropwise and the mixture is heated to reflux for 2 h. It is allowed to cool to 40° C., a red-violet solid (28.6 g) is filtered off and the mother liquor is concentrated. The residue is washed with water and dried to give 16.4 g (84.5 mmol, 38%) of the abovementioned triazine.

Example 4

2-Amino-4-methoxy-6-trifluoromethyl-1,3,5-triazine 41.4 g (0.1 mol) of the copper complex from Example 3 are initially introduced into 300 ml of DMF and 51.2 g (0.4 mol) of methyl trifluoroacetate are added dropwise at 20° C. in the course of 15 min. The mixture is then warmed at 50° C. for 1 hour and at 90° C. for 5 hours. The blue reaction solution is concentrated and the residue is stirred with 100 ml of water and 100 ml of dilute hydrochloric acid. After filtering the suspension with suction, washing the filter cake and drying the residue, 23.4 g (0.12 mol, 60%) of the abovementioned triazine are obtained in the form of a colorless powder.

Example 5

2-Amino-4-ethoxy-6-trifluoromethyl-1,3,5-triazine 8.4 g (0.1 mol) of cyanoguanidine and 35.5 g (0.25 mol) of ethyl trifluoroacetate are initially introduced into 46 g of ethanol, and a suspension of 8.5 g (0.125 mol) of sodium ethoxide in 39.8 g of ethanol is added in the course of 5 min. After the addition of 5.66 g (0.05 mol) of calcium chloride, the reaction mixture is heated to reflux for 7 hours. 0.5 ml of a conc. hydrochloric acid is then added at 20° C. and the ethanol is removed. 100 g of water are added and the suspension is filtered with suction. The residue is washed with 50 ml of water and dried at 50° C./20 mbar. 18.6 g (0.089 mol, 89%) of 2-amino-4-ethoxy-6-trifluoromethyl-1,3,5-triazine are obtained in the form of a colorless powder (HPLC: 99.8 area %, m.p. 124°–125° C.).

Example 6

2-Amino-4-difluoromethyl-6-methoxy-1,3,5-triazine

A solution of 1.9 g (23 mmol) of N-cyanoguanidine and 2.6 g (23 mmol) of calcium chloride in 50 ml of methanol is stirred under reflux for 90 min. The reaction mixture is cooled to from 20° to 25° C. and 5.0 g (45 mmol) of methyl difluoroacetate are rapidly added dropwise, then 4.1 g (23 mmol) of sodium methoxide solution (30 percent by weight in methanol) are slowly added dropwise, whereupon a white precipitate separates. After stirring under reflux for 2 hours, the volatile constituents are removed in a water-jet vacuum at a bath temperature of 40° C., the residue is partitioned between 100 ml of water and 100 ml of ethyl acetate, and the organic phase is separated off and dried over $MgSO_4$. After removal of the solvent at 40° C. in a water-jet vacuum, the title compound remains as a slightly contaminated oil (1.1 g, 6.3 mmol; 28% of theory) which if required can be crystallized by trituration with an ether/hexane mixture (v:v=1:3). $^1$H-NMR spectrum (400 MHz, $CDCl_3$, int. TMS, δ (ppm)): 7.44 br (1 H); 6.97 br (1 H); 6.27 t ($^2J_{H-F}$=55 Hz, 1 H); 3.96 s (3 H). $^{13}$C-NMR spectrum (100 MHz, $CDCl_3$/ $CD_3S(O)CD_3$, int. TMS, δ (ppm), proton-decoupled): 171.5 s (C-$OCH_3$); 169.8 t (C-$CHF_2$, $^2J_{C-F}$25 Hz [sic]); 168.8 s (C-$NH_2$); 111.3 t ($CHF_2$, $^1J_{C-F}$243 Hz [sic]); 54.7 s ($OCH_3$).

We claim:

1. A process for preparing asymmetrically substituted triazines of the formula I

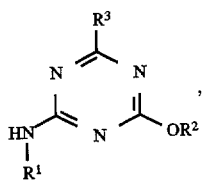

where $R^1$ is hydrogen, methyl or ethyl, $R^2$ and $R^3$ independently of one another are radicals selected from the group consisting of $C_1$–$C_8$-alkyl, $C_3$–$C_8$-alkenyl, $C_3$–$C_8$-alkynyl, $C_3$–$C_8$-cycloalkl, phenyl, benzyl and phenethyl, by reaction of a cyanoguanidine of the formula II

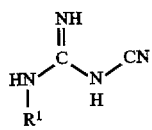

which a carboxylic acid derivative in the presence of an alcohol of the formula III

$$R^2\text{—OH} \qquad \text{III,}$$

which comprises reacting a carboxylic acid ester of the formula IV

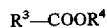

$$R^3\text{—COOR}^4 \qquad \text{IV,}$$

where $R^3$ has the abovementioned meaning and $R^4$ is a radical selected from the group consisting of $C_1$–$C_8$-alkyl, $C_3$–$C_8$-alkenyl, $C_3$–$C_8$-alkynyl, $C_3$–$C_8$-cycloalkyl, phenyl, benzyl and phenethyl, in the presence of a base or of a carboxamide selected from the group consisting of N,N-di ($C_1$–$C_4$-alkyl)formamide, N,N-di-($C_1$–$C_4$-alkyl)acetamide and N-methylpyrrolidone and in the presence of salt of the elements magnesium, calcium, aluminum, zinc, copper, iron, cobalt, nickel or chromium.

2. A process as defined in claim 1, wherein the base used is an alkoxide or a tertiary amine.

3. A process as defined in claim 1, wherein the base used is an alkali metal alkoxide or alkaline earth metal alkoxide of the alcohol III.

4. A process as defined in claim 1, wherein the abovementioned elements are employed in the form of their halides, nitrates, sulfates, alkoxides or acetates.

5. A process as defined in claim 1, wherein the salts as in claim 1 are used in an amount of from 0.001 to 2 mol per mole of cyanoguanidine II.

6. A process as defined in claim 1, wherein the salts of heavy metals are used in less than stoichiometric amounts, based on the cyanoguanidine II.

7. A process as defined in claim 1, wherein salts of the alkaline earth metals calcium or magnesium are used.

8. A process as defined in claim 6, wherein the alkaline earth metal compounds are used in an amount of from 0.01 to 2 mol per mole of cyanoguanidine II.

9. A process as defined in claim 1, wherein the carboxylic acid esters used are the $C_1$–$C_6$-alkyl esters of a perfluorinated or perchlorinated $C_1$–$C_3$-carboxylic acid.

10. A process as defined in claim 1, wherein methyl trifluoroacetate is reacted in methanol in the presence of an alkali methoxide as a base.

11. A process as defined in claim 1, wherein methyl trifluoroacetate is reacted with a cyanoguanidine II in the presence of an alkali methoxide and of a calcium salt.

12. A process as defined in claim 1, wherein methyl trifluoroacetate is reacted with the cyanoguanidine II in N,N-dimethylformamide in the presence of copper salts.

13. A process as defined in claim 1, wherein methyl trifluoroacetate is reacted with a cyanoguanidine II in the presence of an alkali methoxide and of a zinc salt.

* * * * *

UNITED STATES PATENT AND TRADEMARK OFFICE
CERTIFICATE OF CORRECTION

PATENT NO.: 5,739,328

DATED: April 14, 1998

INVENTOR(S): SCHAEFER et al.

It is certified that error appears in the above-identified patent and that said Letters Patent is hereby corrected as shown below:

Column 8, claim 1, line 19, "cycloalkl" should be --cycloalkyl--.

Column 8, claim 5, line 54, delete "as in claim 1".

Column 8, claim 6, line 57, delete "the".

Signed and Sealed this

Seventh Day of July, 1998

*Attest:*

BRUCE LEHMAN

*Attesting Officer*    *Commissioner of Patents and Trademarks*